(12) United States Patent
Kroll et al.

(10) Patent No.: US 6,408,206 B1
(45) Date of Patent: Jun. 18, 2002

(54) DISPOSABLE EXTERNAL DEFIBRILLATOR

(75) Inventors: Mark W. Kroll, Simi Valley, CA (US); Kai Kroll, Minneapolis; Karl J. F. Kroll, Maple Grove, both of MN (US)

(73) Assignee: Kroll Family Trust, Simi Valley, CA (US)

(*) Notice: Subject to any disclaimer, the term of this patent is extended or adjusted under 35 U.S.C. 154(b) by 0 days.

(21) Appl. No.: 09/510,916

(22) Filed: Feb. 22, 2000

Related U.S. Application Data

(63) Continuation-in-part of application No. 09/061,755, filed on Apr. 16, 1998, now Pat. No. 6,041,255.

(51) Int. Cl.[7] .................................................. A61N 1/39
(52) U.S. Cl. ........................................................ 607/5
(58) Field of Search ............................................ 607/5

(56) References Cited

U.S. PATENT DOCUMENTS

| | | | |
|---|---|---|---|
| 5,545,184 A | 8/1996 | Dougherty | 607/5 |
| 5,635,812 A | 6/1997 | Eschback et al. | 320/1 |
| 5,919,211 A | 7/1999 | Adams | 607/5 |

Primary Examiner—William E. Kamm

(57) ABSTRACT

A pocket-sized disposable external defibrillator relies on the use on a thermal battery which using a pyrotechnic molten salt electrolyte which delivers an extremely high current for a short period of time thus providing a perfect energy source for a rare use of an external disposable defibrillator.

22 Claims, 14 Drawing Sheets

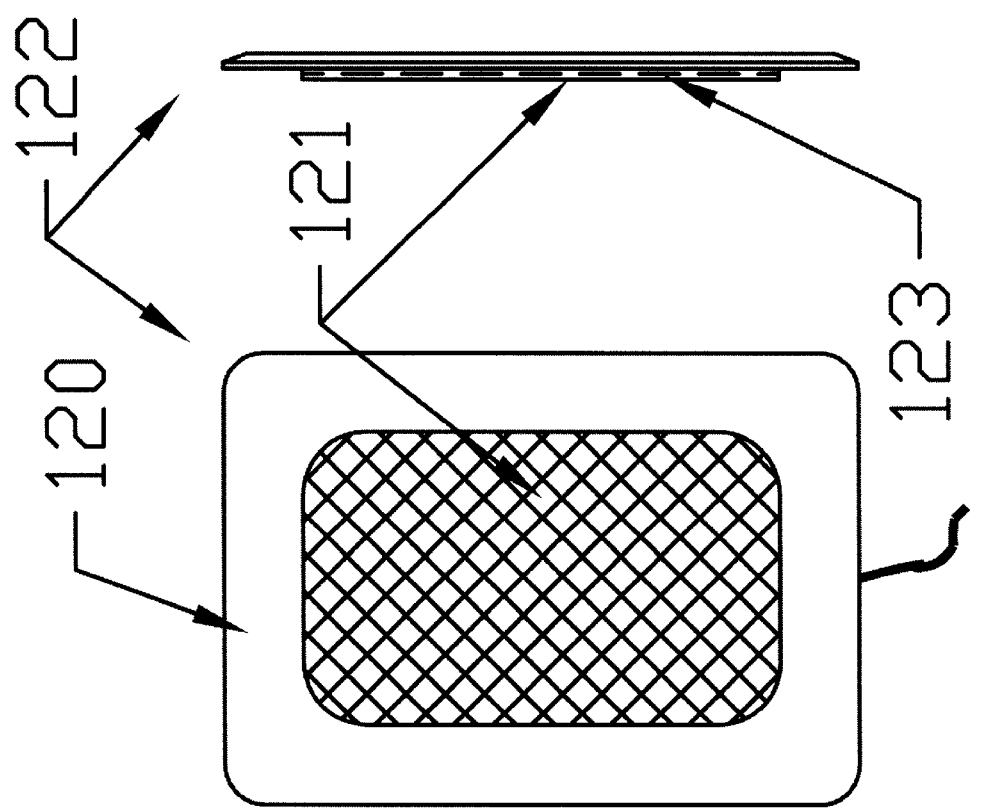

DISPOSABLE EXTERNAL DEFIBRILLATOR

This application is a continuation-in-part of "Disposable External Defibrillator" U.S. Ser. No. 09/061,755 filed on Apr. 16, 1998 now U.S. Pat. No. 6,041,255.

BACKGROUND OF THE INVENTION

External defibrillators are well known in the art and play a very critical role in resuscitation of cardiac arrest victims. However, these devices remain fairly expensive, heavy, and large. No practical disposable external defibrillator has been taught. No practical pocket size defibrillator has been taught.

BRIEF DESCRIPTION OF THE DRAWINGS

FIG. 14: Details of the outer side embodiment patches.

DETAILED DESCRIPTION OF THE DRAWINGS AND PREFERRED EMBODIMENT

Figure 1:
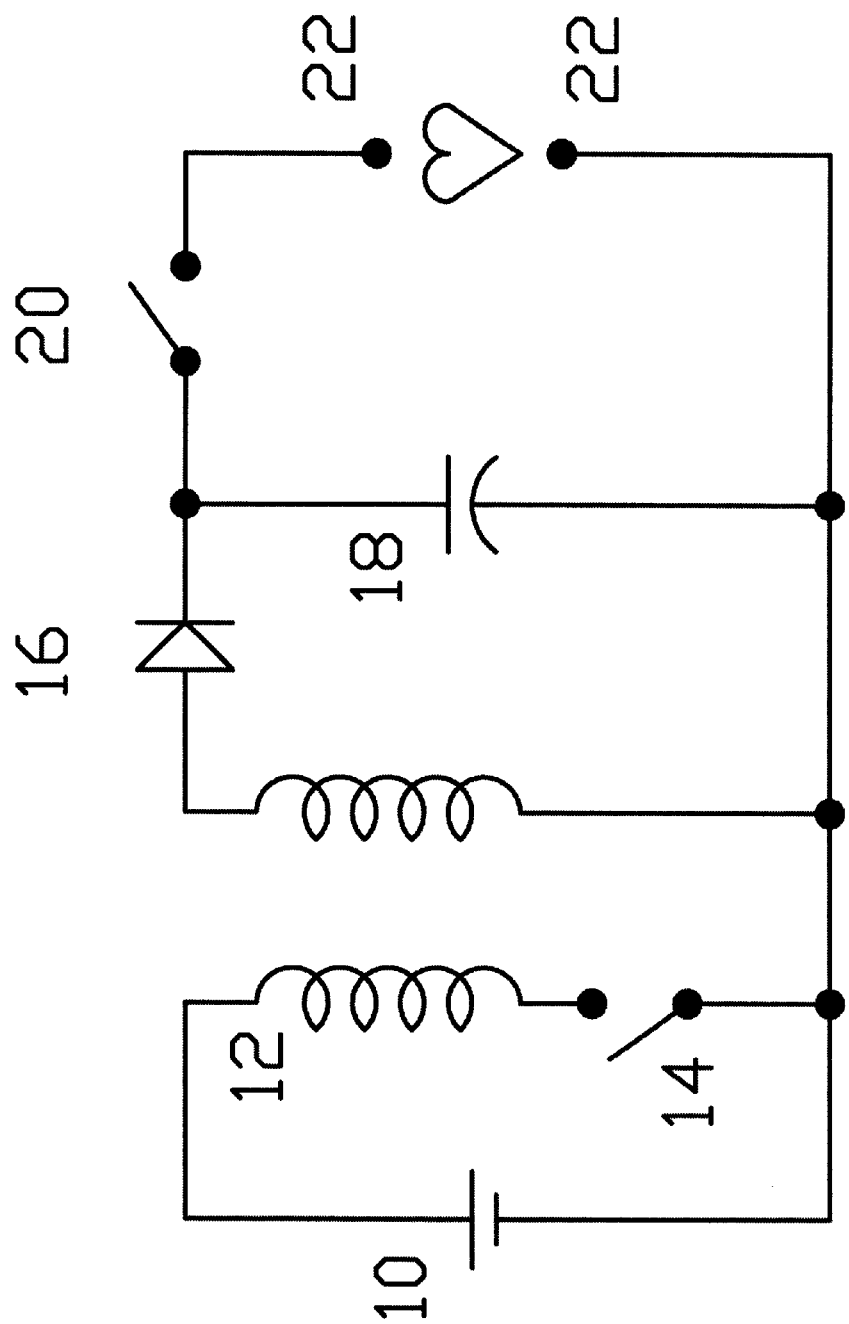
FIG. 1: Simplified schematic of an external defibrillator.

FIG. 1 shows the schematic for a basic external defibrillator as is well known in the art. Battery 10 supplies current through the primary winding of transformer 12 on an interrupted basis given by the cycling of switch 14. This results in a high-voltage output from the secondary of transformer 12 which is captured by diode 16 and stored in capacitor 18. When it is desired to deliver a shock switch 20 is closed thus delivering the high voltage and high current from capacitor 18 to electrodes 22 attached to the victim's chest.

This is a highly simplified schematic of the external defibrillator. Many embellishments are possible. For example, switch 20 can be replaced by a set of four switches to deliver a biphasic shock to electrodes 22 for increased performance. These embellishments are not critical to the operation of the instant invention, but could be added.

What is important is that the battery 10 and capacitor 18 are very large components. The battery 10 must deliver sufficient current to charge up capacitor 18 in a very short time. Preferably, this is under 10 seconds. Capacitor 18 must be capable of storing a large amount of energy, on the order of that in a small rifle cartridge or about 200–400 joules. The size of these components has limited the reductions in size and weight of present external defibrillators. There are some teachings of improved capacitors for defibrillatons. These are primarily directed towards implantable defibrillators which are extremely small and have much less energy. There is a U.S. Pat. No. 5,545,184 of Dougherty entitled "Cardiac Defibrillator with High Energy Storage Anti-Ferroelectric Capacitor" that teaches the use of a ceramic "anti-ferroelectric" capacitor with high energy storage properties. Hence, this involves the use of heavy metals such as lead, zirconium and it is not clear how this could reduce the weight of an external defibrillator.

Figure 2:
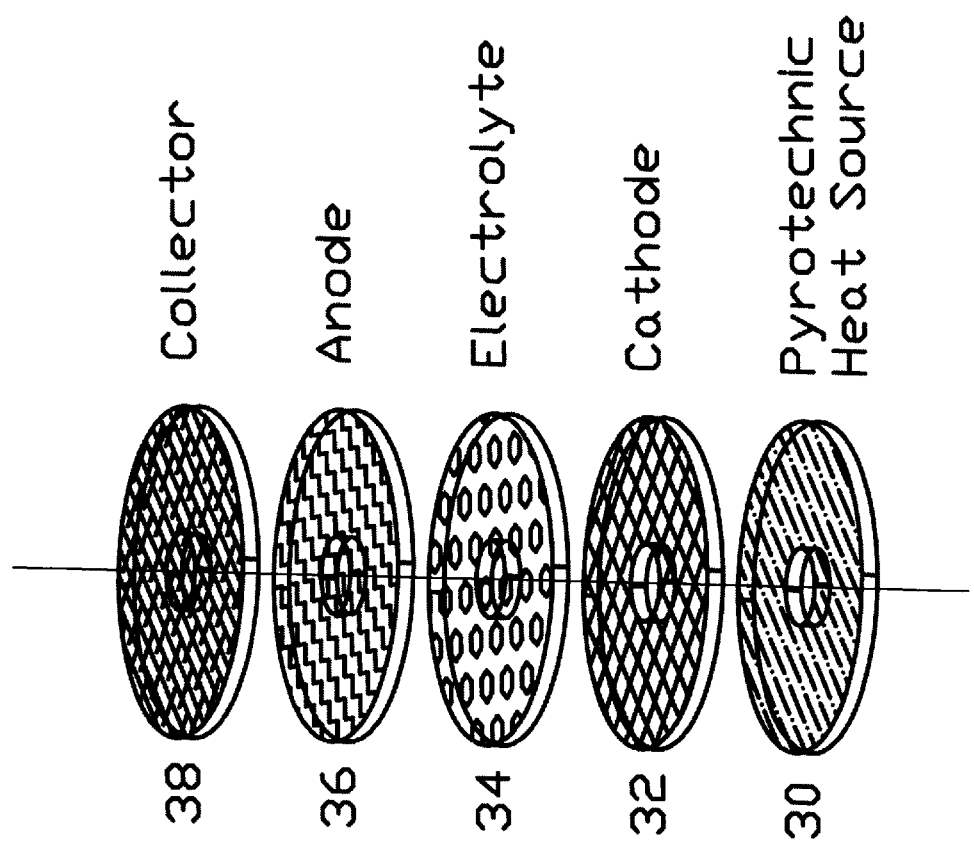
FIG. 2: Internal construction of a thermal battery pile.

One of the elements of this invention is the use of a thermal battery for battery 10. These batteries have been used primarily in military applications such as missiles and artillery shells. The detailed construction of the piles of a thermal battery is shown in FIG. 2. It begins with a pyrotechnic heat source 30 which is followed by a cathode 32 which is followed by an electrolyte 34 followed by an anode 36 followed by a current collector 38. The electrolyte at normal ambient temperatures is a solid non-conducting inorganic salt. The electrolyte is rendered molten by the pyrotechnic heat source. The heat melts the electrolyte which causes it to be conductive and deliver electrical power at an extremely high rate. The thermal battery has many attributes making it ideal for an external defibrillator. First, it has no leakage current until it is triggered. It then delivers current at a very high rate for a short period of time on the order of minutes to an hour at the maximum.

Representative materials for the battery anode include lithium, calcium, magnesium, and others. The electrolytes that have been used successfully in these batteries have been lithium chloride and potassium chloride mixtures primarily. Representative cathodes are $FeS_2$, $K_2Cr_2O_7$, $WO_3$, $CaCrO_4$, and $V_2O_5$ for example. A typical pyrotechnic heat source is iron with $KClO_4$.

Figure 3:
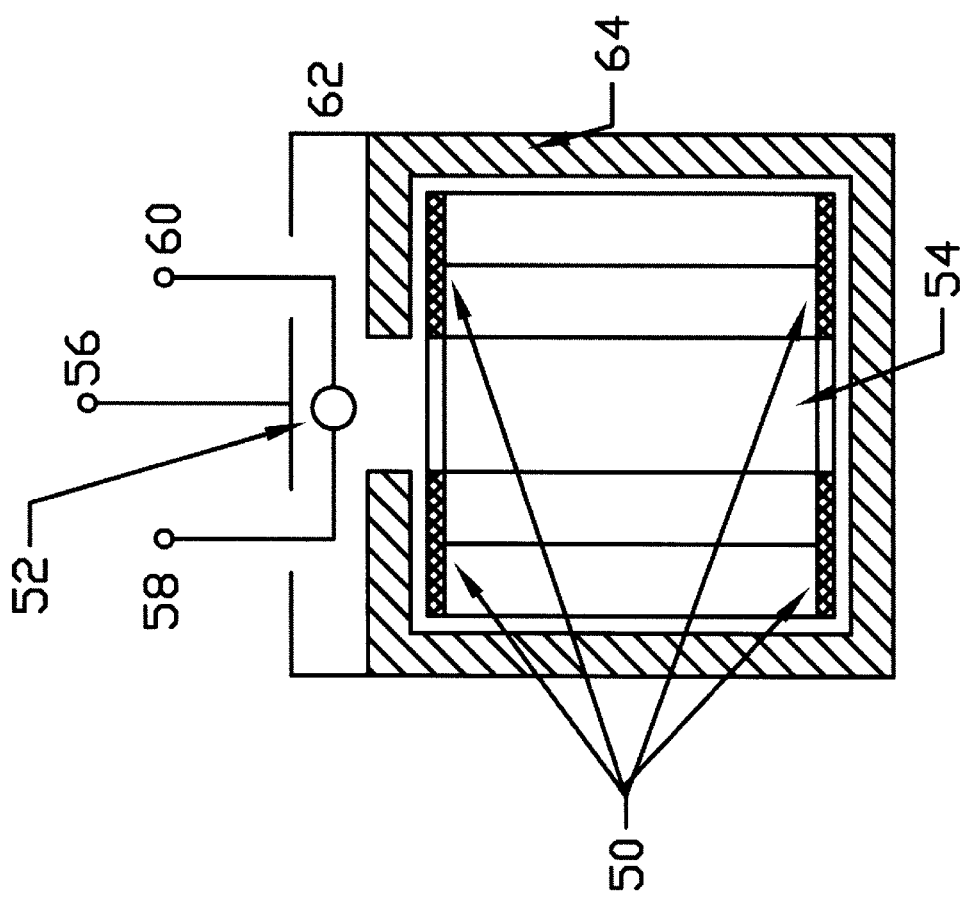
FIG. 3: Basic design of a complete thermal battery.

FIG. 3 shows the overall construction of a thermal battery. Battery piles 50 are shown stacked as disks leaving an open core area 54. The electric match 52 is placed above that open core area and is used to heat the battery to begin the process. Electric match 52 is ignited through current passing through electrodes 58 and 60. Connection 56 is used for delivery of current from the battery and the other connection can be one of the match terminals, either 58 or 60. As an alternative, yet a fourth electrode could be used for the battery output current. Insulation material 64 is wrapped around the battery to keep it very hot so it can achieve its high levels of efficiencies. Temperatures on the order of 230° Celsius are not uncommon. Representative insulation that can be used include Mica, Silicon-bonded Mica, FiberFrax™, Microtherm™, Aluminum/Mica combinations, and Min-K™. Other representative advanced insulation materials include MA-25 and MI-15 from Lockheed Martin Thermal Protection Products (www.lmco.com/michoud/thermal.htm).

Thin blankets of polyamide film or beta cloth can be used to encapsulate fiberglass to form an outer layer used in conjunction with inner blanket layers of metal deposited films and dacron mesh. Such composite insulators are available from HiTemp Insulation (www.hitempca.com/docs/space.html.

Figure 4:
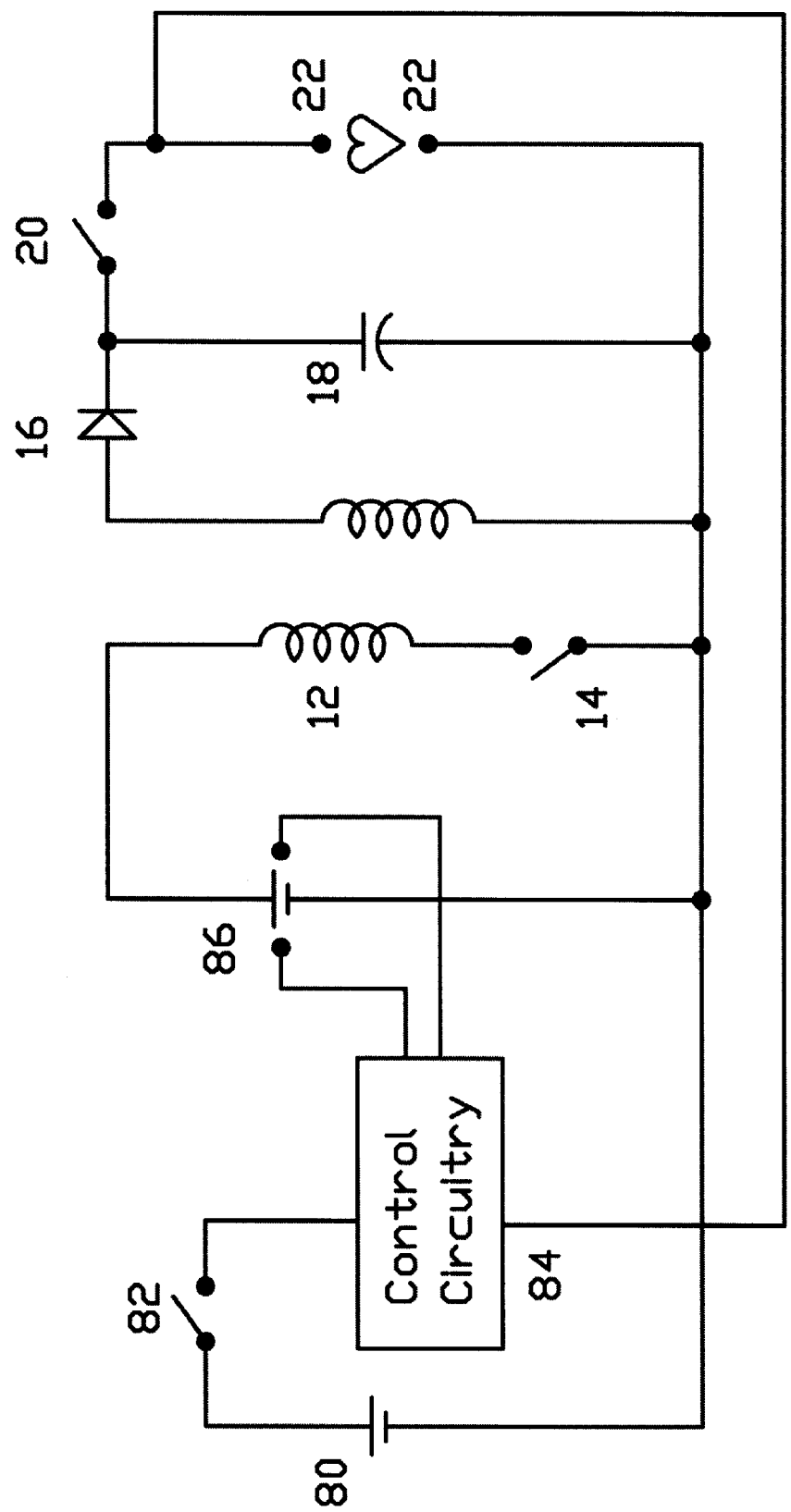
FIG. 4: Schematic of a preferred embodiment of the instant invention.

FIG. 4 shows a simplified schematic for the disposable external defibrillator envisioned by this invention. The thermal battery 86 is shown with the connections on the sides for the electric match triggering. Suitable batteries are Models EAP-12009 and EAP-12024 from Eagle-Picher Industries of Joplin, Mo. Thermal batteries are also available from Sandia Labs of Albuquerque, N.Mex.

A conventional non-thermal small battery 80 will deliver current when switch 82 is activated to control circuitry 84. Battery 80 could be from a large family of non-thermal batteries including high-current lithium batteries, manganese dioxide, or (for cost concerns) alkaline and carbon-zinc batteries. That current is then delivered to the electric match connections of thermal battery 86. That will cause the thermal battery 86 to go into its high-temperature mode and deliver current at an extremely high level. The rest of the operation of the external defibrillator is fairly standard at this point. The current from the thermal battery 86 is then used to deliver current through the transformer primary 12 by the interrupted on-off action of switch 14. That results in a high-voltage output from transformer 12 which is captured by diode 16 and stored in capacitor 18. The output from capacitor 18 is then delivered to the victim's electrodes 22 by the closure of switch 20. Shock voltages range from 1,000 to 5,000 volts with a preferred range of 1,400–4,000 volts. This is the voltage stored on the capacitors and is also the peak waveform voltage.

One of the disadvantages of the thermal batteries is that they become very hot when they are in use. This can actually be an advantage for the external defibrillator as many types of capacitors become more efficient at higher temperatures. For example, so-called photoflash capacitors and even general aluminum electrolytics become more and more efficient at energy storage at higher temperatures. An extreme example of high temperature capacity efficiencies is seen with a polyvinylidene fluoride capacitor. It can have a change in capacitance value over temperature of up to 10 to 1 as shown in U.S. Pat. No. 5,635,812: Eschback et al, "Thermal Sensing Polymeric Capacitor". Ironically, in that patent the capacitor is attached to a cell phone battery as a high temperature sensor only. It is designed to detect a battery failure as high temperature from a conventional battery is pathologic and thus the invention does not teach the intentional heating of a capacitor to increase its efficiencies.

An AED should store between 200 and 400 joules in its output capacitors. With an energy density range of 1.8–4 joules per cubic centimeter the volume range for the AED output capacitors will be 50–222 milliliters or 3.05–13.54 in$^3$. In a attempt to make smaller AEDs with conventional components, some manufacturers have made the controversial choice of taking the energy down to only 150 joules. This decreases the capacitor volume to 37.5–83 ml or 2.3–5.1 in$^3$.

Figure 5:
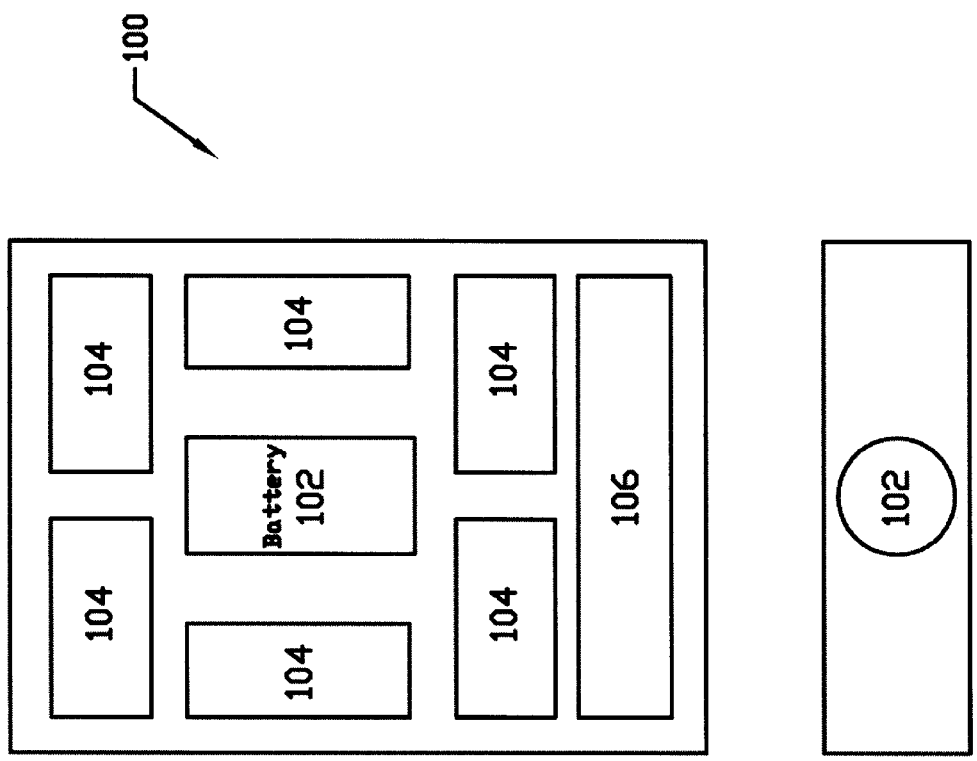
FIG. 5: Typical layout of one embodiment of the invention

FIG. 5 shows a possible mechanical layout of the preferred embodiment of the device. The basic external defibrillator 100 begins with the thermal battery 102 in the center of the unit which is then surrounded by six aluminum electrolytic capacitors 104. Finally the control circuitry 106 is shown at the bottom. This allows for the temperature of the thermal battery to increase the energy storage capabilities of the capacitors 104.

The EAP-12009 thermal battery delivers about 3,000 joules and would thus be capable of delivering about 10 shocks. Its rated life is only 65 seconds which is sufficient for the typical rescue but this could be extended by adding insulation which would slightly increase the AED volume. It weighs about 1 pound and has a volume of 9.76 cubic inches. The EAP-12024 delivers about 30,000 joules and has a life of about 16 minutes. Thus it could provide about 100 shocks over a lengthy resuscitation attempt. It has a weight of 1.7 pounds and a volume of about 17 cubic inches. A 16 minute battery life is sufficient to allow for the arrival of backup paramedics (with conventional defibrillators with more shocks and operating time) in almost all situations.

Using the rule-of-the-thumb that the battery is 50% of the weight and 40% of the volume suggests that a practical AED using these batteries would have a weight range of 2–3.4 pounds and volume range of 24.4–42.5 in$^3$.

A smaller device could be made with the EAP-12001M. This delivers about 2,800 joules and has a lifetime of 85 seconds. It weighs 250 grams and has a volume of 6.28 in$^3$. This could be used to make an AED with a weight of 500 grams (1.1 lbs.) and a volume of 15.7 in$^3$. Another small thermal battery is the model MC3246 available from Sandia Laboratories. It has a volume of 3.53 in$^3$ and a weight of 0.44 pounds.

Figure 6:
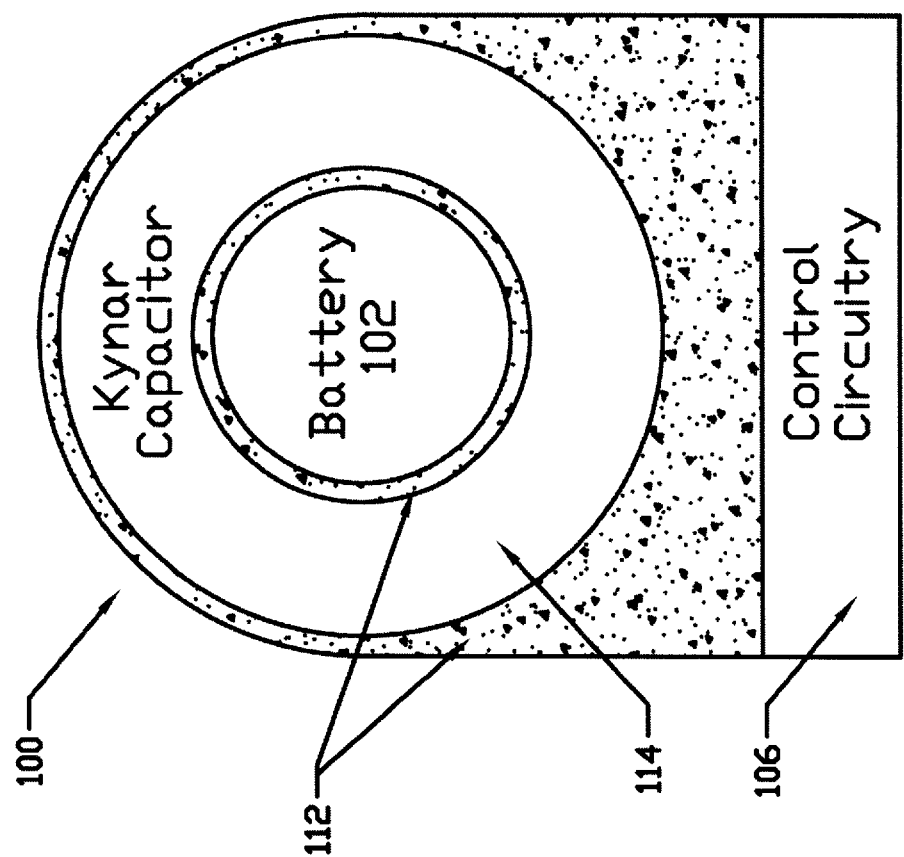
FIG. 6: Typical layout of another embodiment of the invention.

Another embodiment is shown in FIG. 6. Here the battery 102 is surrounded by a thin layer of insulation 112. Wrapped around that is a polyvinylidene fluoride capacitor which is also known by the tradename Kynar™. That in turn is surrounded by more insulation 112. Finally the control circuitry 106 is shown on the side of this cylindrical construction. This results in a largely cylindrical external defibrillator 110.

Figure 7:
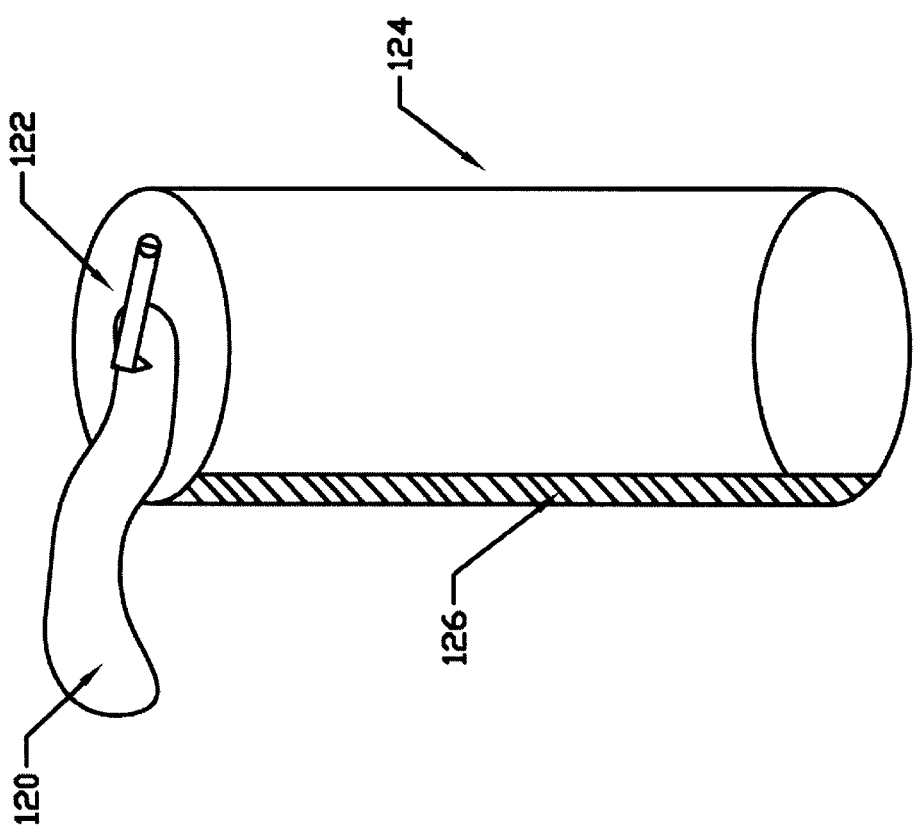
FIG. 7: Field packaging for the second embodiment of the instant invention.

FIG. 7 shows a final field packaged embodiment of the device. In this illustrative example we are assuming the cylindrical packaging of FIG. 6. Here a vapor proof seal, preferably a metallic or plastic film 124 is completely wrapped around the device. A pulltab 120 is attached to the top of the external defibrillator. When the pulltab 120 is pulled, the springloaded striker hammer 122 will be driven down into a primer on a thermal battery. This is an alternative method of igniting a thermal battery instead of using the electric match. This primer is similar to that seen on a shotgun. It would then begin the ignition process without the need for an ancillary battery such as battery 80 shown in FIG. 4. Pulling, the pulltab 120 further down will tear open strip 126 thus removing the jacket completely from the can. This also would allow for the placement of the electrodes within the jacket. This would keep the electrodes protected from the environment and from drying out.

Alternatively, the hammer 122 could be replaced by a conventional microswitch and conventional small battery. Thus when pulltab 120 was pulled the non-thermal battery would deliver current to the electric match to ignite the thermal battery as shown in FIG. 4.

Many variations could be made on this basic invention. For example, an additional small battery which is a small 3-volt alkaline cell or lithium cell could be used for monitoring and data storage. When the device was opened up and turned on in this embodiment, the user would not have to commit to using the thermal battery which is, after all, a single-use battery. The small battery would then just be used to monitor the patient's rhythm to decide whether or not a shock was needed.

In yet another alternative embodiment a non-volatile RAM (random access memory) could be used for the data logging. This could be used when only the thermal battery was present. Thus, after the thermal battery was expended, data recording the patient's rhythm and action of the shock would still be saved.

This approach of the thermal battery could also be used for everything from a fully manual operation to fully automatic operation of the external defibrillator. The thermal battery could be made removable and thus it would be disposed of after usage. The remaining portion of the AED would simply receive a new thermal battery to restore it to fully operational status.

Figure 8:
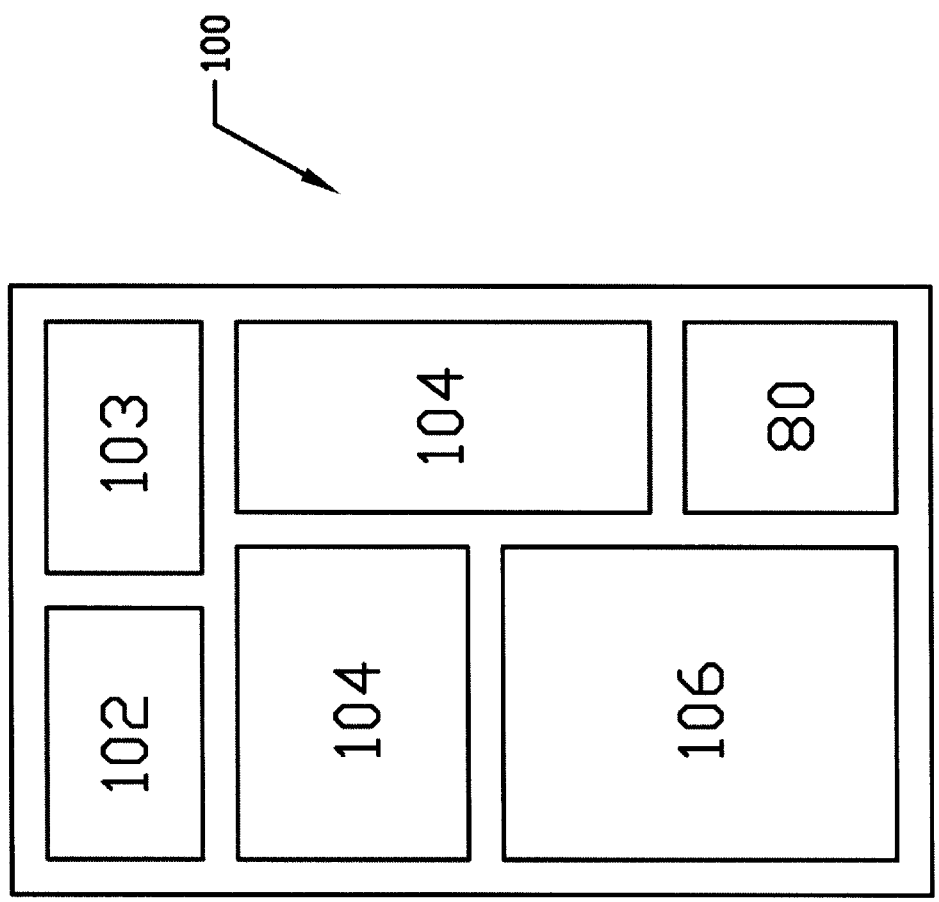
FIG. 8: Embodiment with dual thermal batteries.

FIG. 8 shows an embodiment of a disposable defibrillator 100 utilizing multiple thermal batteries 102 & 103. The thermal batteries charge output capacitors 104 with then help of control and monitoring circuitry 106 and monitoring battery 80. One of the disadvantages of thermal batteries is the short discharge life. Larger thermal batteries may be designed to run to an hour or more, but typically they last for a few minutes. For use in an automatic external defibrillator, the battery must run for approximately 10 minutes. A thermal battery required to last ten minutes requires more insulation than a two-minute battery. Multiple batteries solve this problem. The first battery may last 2 minutes providing the energy for 3 shocks each of 150 J. The energy required for the first battery is then approximately 500 J allowing for inverter inefficiency. The second battery 103 is a 1000 J thermal battery able to deliver three 300 J shocks.

Figure 9:
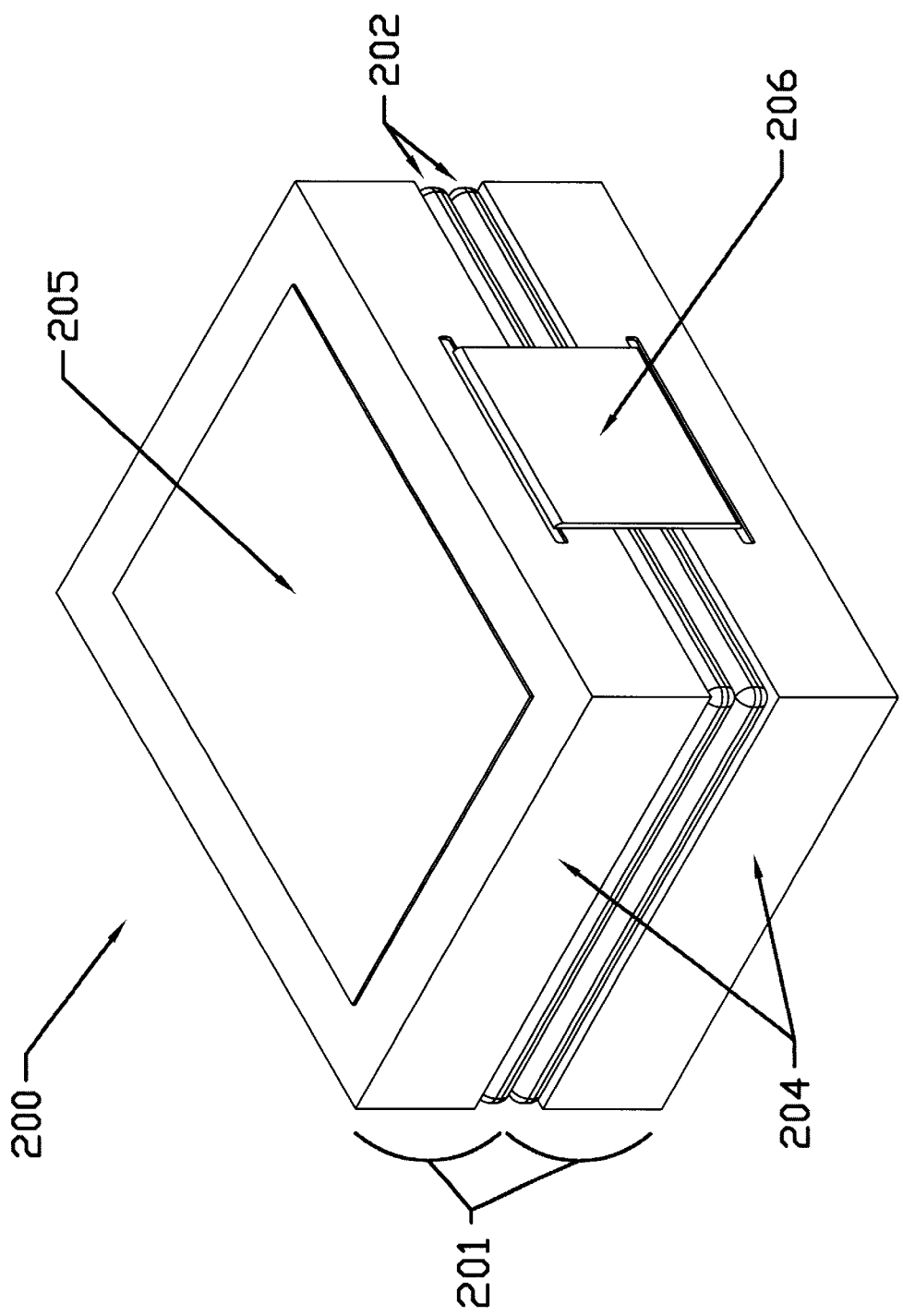
FIG. 9: Embodiment with split case.

FIG. 9 shows a novel method of storing electrodes within a disposable defibrillator. The defibrillator 200 is composed of two halves 201 that open like a book. Electrodes 202 are fixed to the housing 204 containing the electronics. Membrane keypad and display 205 is opposite the electrode on one half 201. The electrodes are protected in the center when the halves are closed. Flat cable 206 is expandable and provides electrical communication between the halves. The cable is stored in one of the halves or outside the halves. The halves are shown as roughly equal in size however, they typically would be unequal in thickness. For example, one half would hold the thermal batteries and capacitors while the other would hold the control circuitry and monitoring battery. This has the advantage of keeping temperature sensitive components isolated from the hot thermal batteries.

Figure 10:
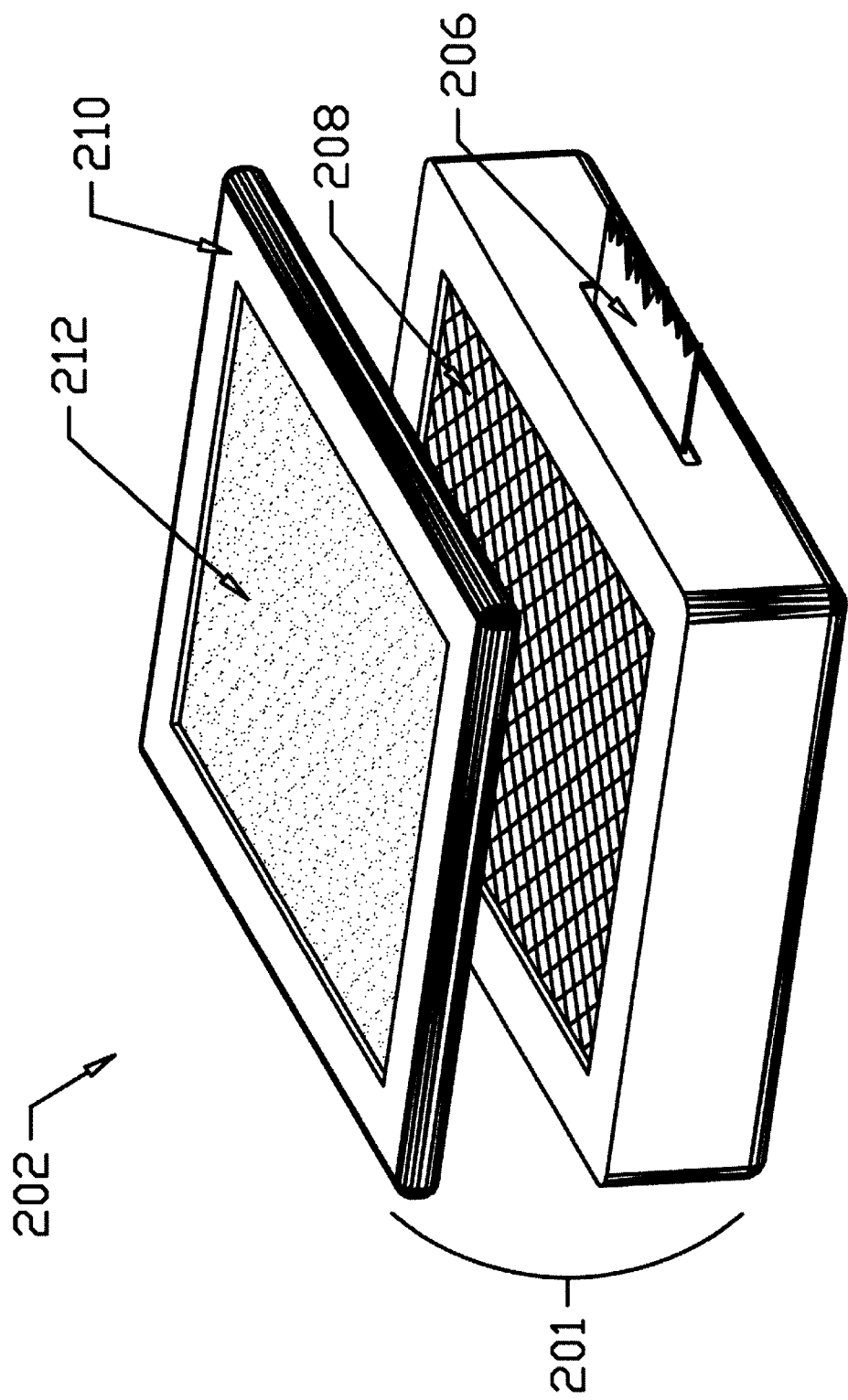
FIG. 10: Split case embodiment electrode details.

FIG. 10 shows the assembly of one of the halves 201. Electrode 202 is composed of an outer padded adhesive ring 210 and conductive gel 212. Housing 204 has a conductive screen 208 that conducts the current to the gel that is in contact with the patient's chest. Flat cable 206 is shown protruding from the housing.

Figure 11:
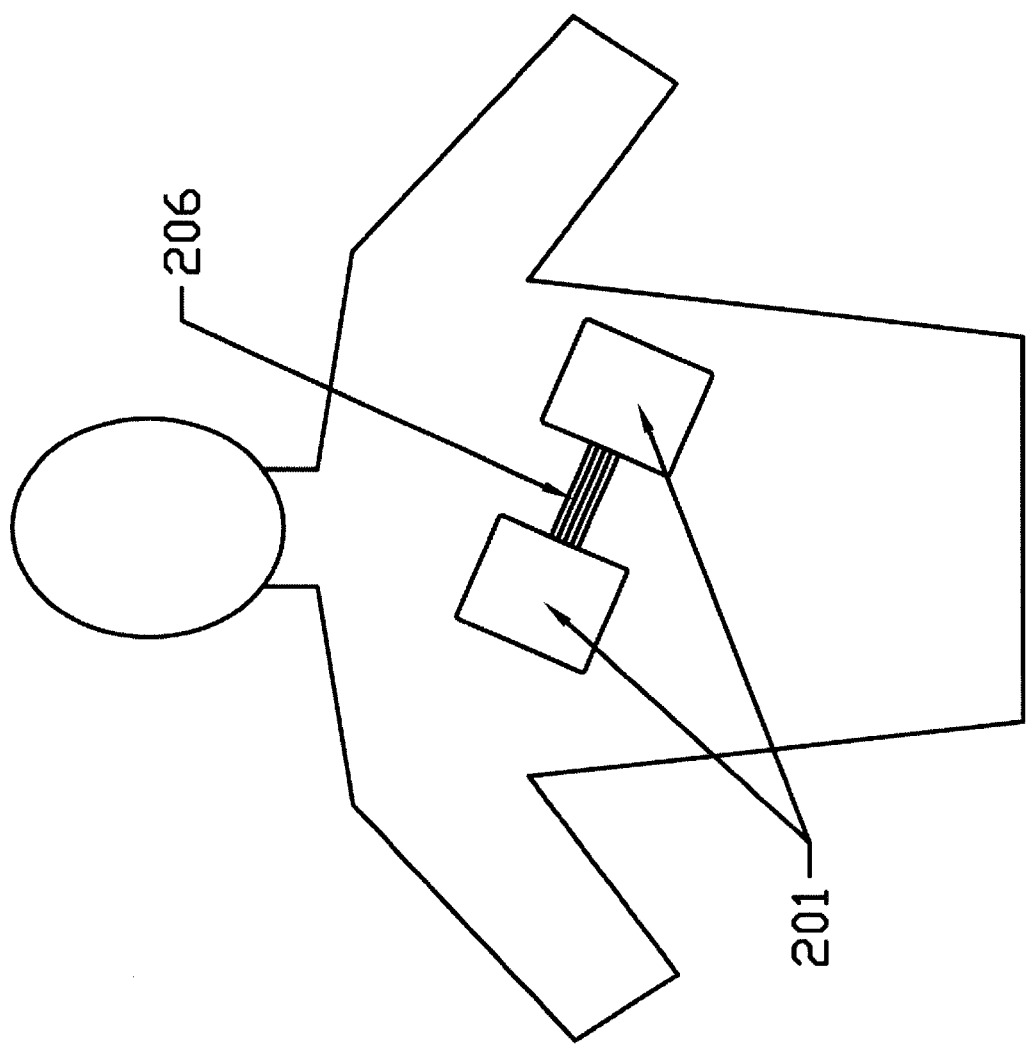
FIG. 11: Embodiment with split casein operation.

FIG. 11 shows the disposable defibrillator attached to a patients chest. Separate halves 201 are fixed to the patient in an optimal fashion and the cable 206 conducts between them.

Defibrillators are often in dirty or wet environments. To reduce the chance of a defibrillator failing due to water or some other foreign matter, in an alternative embodiment, the patches used in defibrillation are used to seal the controls and other components of a defibrillator. The patches are "stuck" to the outside of the defibrillator with adhesive that is around the perimeter of the pad. The surface of the defibrillator, under the pads, could be kept as level as possible to reduce the chance that a foreign object may tear or pierce the pad. Thin strong sheets of plastic could also be an integral part of the patch to reduce the chance of an unintentional perforation.

Figure 12:
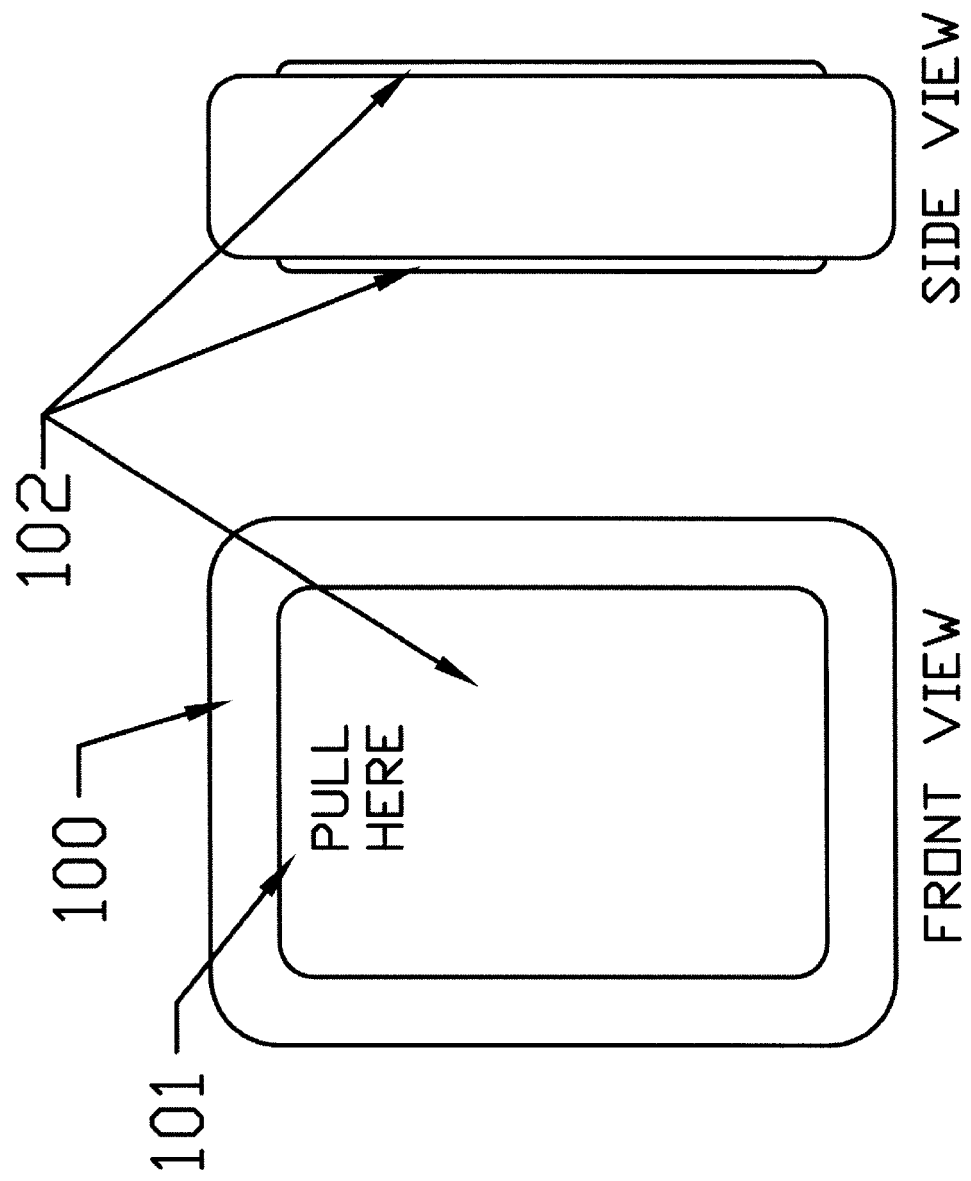
FIG. 12: Embodiment with flat electrodes on outer sides of device.

In FIG. 12 the defibrillator 100 and patches 102 are adhered to the sides of the defibrillator. The patches could have adhesive around the perimeter of the pad for example. One edge, or corner 101 of the patches is labeled to indicate how to remove the patches.

Figure 13:
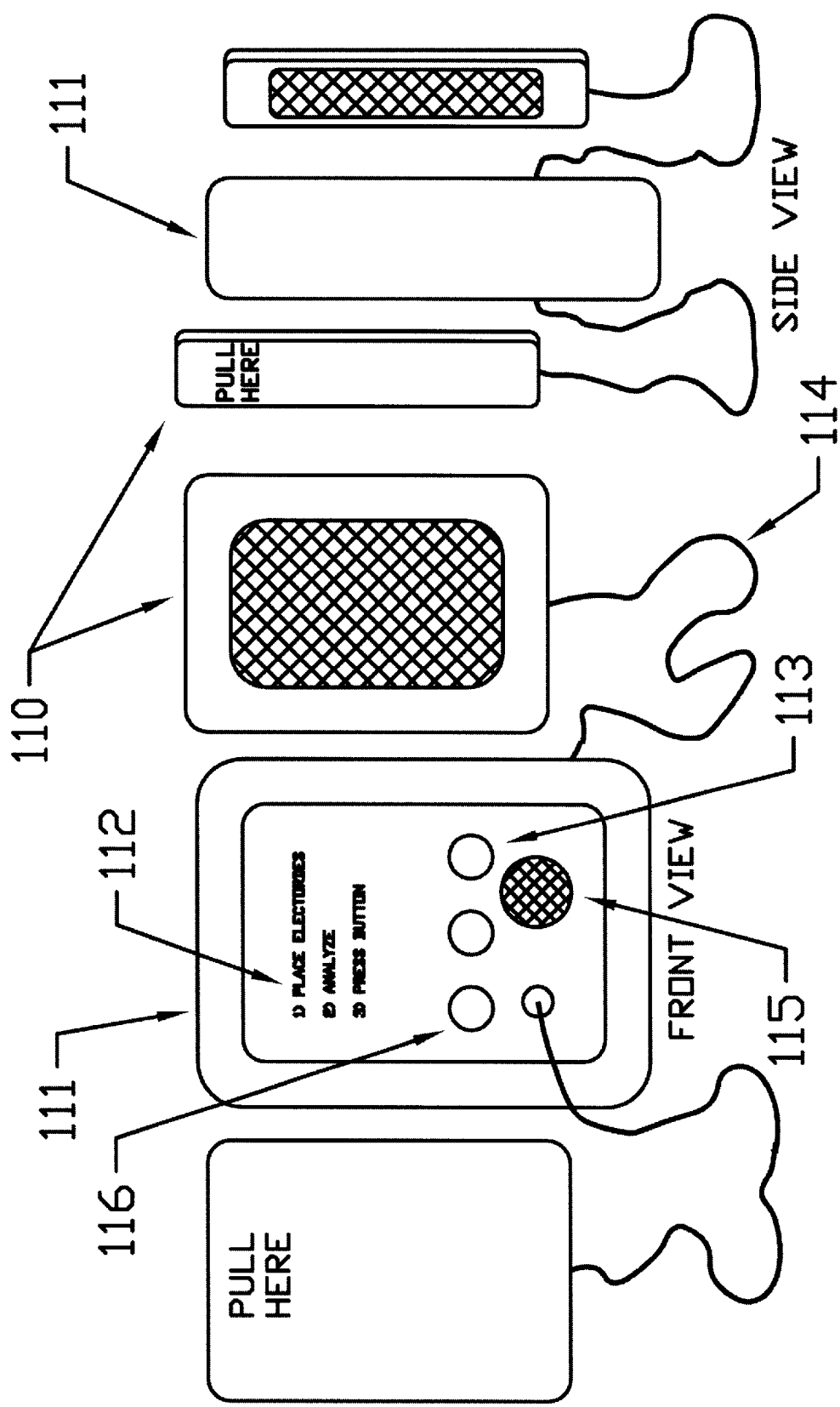
FIG. 13: Details of the outer side embodiment layout.

In FIG. 13 the patches are removed revealing the controls placed underneath the patches. The patches 1110 have been removed from the defibrillator body 111. The cables 114 and controls 113, speaker or other audio source 115, displays 116 are now accessible and ready for use. Printed instructions 112 are placed underneath the patches.

A detail view of a patch is shown in FIG. 14. The adhesive 120 around the perimeter of the complete patch 122 is used to attach the patch to the defibrillator. The gel 121 is protected from the elements because the gel is on the inside of the complete defibrillator. The gel could also be in contact with a conductive material, so that electrical current could be passed through to test the condition of the gel. A patch strengthener 123 could be an integral part of the patch to reduce the chance of damage from sharp objects or abrasion.

We claim:

1. An electronic apparatus consisting of a nonactivated battery, a capacitor in thermal communication with the battery, and a charging system electrically communicating with both the battery and the capacitor, so that the nonactivated battery provides the electrical energy to charge a capacitor as well as the thermal energy to elevate it to a temperature for more efficient operation.

2. The apparatus of claim 1 in which the electronic apparatus is an external defibrillator.

3. The apparatus of claim 1 in which the capacitor is made of polyvinylidene fluoride.

4. The apparatus of claim 1 in which the capacitor is an aluminum electrolytic type.

5. The apparatus of claim 1 in which the capacitor is charged to a voltage of between 1,000 and 5,000 volts.

6. The apparatus of claim 1 in which the nonactivated battery is a thermal battery.

7. The apparatus of claim 6 in which the thermal battery uses an electrolyte chosen from the set of LiCl, KCl, and a mixture of LiCl and KCl.

8. The apparatus of claim 6 in which a conventional battery is used to activate the thermal battery.

9. The apparatus of claim 6 in which a percussion primer is used to activate the thermal battery.

10. The apparatus of claim 6 in which a non-volatile memory is used for data storage.

11. The apparatus of claim 6 in which the thermal battery is removable and replaceable.

12. The apparatus of claim 6 in which the defibrillator is operated manually.

13. The apparatus of claim 6 in which the defibrillator allows automatic operation.

14. The apparatus of claim 6 in which the entire apparatus is contained within a vapor proof removable jacket.

15. The apparatus of claim 6 in which the apparatus includes electrodes wrapped around the defibrillator.

16. The apparatus of claim 6 in which the defibrillator is capable of shocks of a stored energy in the range of 150 to 400 joules.

17. The apparatus of claim 6 in which the volume of the defibrillator is in the range of 15.7 to 42.5 cubic inches.

18. The apparatus of claim 6 in which the weight of the defibrillator is in the range of 1.1 to 3.4 pounds.

19. The apparatus of claim 6 in which the thermal battery is mounted to allow for field replacement.

20. The apparatus of claim 6 with at least two thermal batteries.

21. The apparatus of claim 6 in which the defibrillator is composed essentially of two main pieces from each other.

22. The apparatus of claim 6 in which the defibrillator holds its electrodes between the two mechanically separateable pieces.

* * * * *